United States Patent [19]

Krief

[11] Patent Number: 4,487,955
[45] Date of Patent: Dec. 11, 1984

[54] PROCESS FOR PREPARING CIS OR TRANS, OPTICALLY ACTIVE MONOALKYL ESTERS OF CYCLOPROPANE-1,3-DICARBOXYLIC ACIDS

[75] Inventor: Alain Krief, Wepion, Belgium

[73] Assignee: Roussel Uclaf, Paris, France

[21] Appl. No.: 511,506

[22] Filed: Jul. 6, 1983

Related U.S. Application Data

[63] Continuation-in-part of Ser. No. 308,027, Oct. 2, 1981, abandoned, which is a continuation-in-part of Ser. No. 308,026, Oct. 2, 1981, Pat. No. 4,408,066.

[51] Int. Cl.³ .............................................. C07C 69/74
[52] U.S. Cl. .................................................... 560/124
[58] Field of Search ........................................ 560/124

[56] References Cited

FOREIGN PATENT DOCUMENTS 1596030 8/1918 United Kingdom .

Primary Examiner—Michael L. Shippen
Attorney, Agent, or Firm—Charles A. Muserlian

[57] ABSTRACT

A novel process for the preparation of esters of 2,2-dimethyl-cyclopropane-1,3-dicarboxylic acids in their optically active forms having a cis or trans configuration I comprising salifying the monomethyl ester of (1RS,3SR) cis 2,2-dimethyl-cyclopropane-1,3-dicarboxylic acid with d or l α-methyl-benzylamine, recovering the crystallized salt formed, dissolving the said salt in water, treating the solution with a mineral base and then with an acid to obtain either the monomethyl ester of (1R,3S) cis 2,2-dimethyl-cyclopropane-1,3-dicarboxylic acid I or its (1S,3R) cis isomer depending on whether d or l α-methyl-benzylamine, respectively was used, if desired, reacting the latter cis compound with a strong base to isomerize the monomethyl ester to the monomethyl ester of (1S,3S) trans 2,2-dimethyl-cyclopropane-1,3-dicarboxylic acid I or (1R,3R) trans isomer, respectively, or reacting the latter cis compound with a tert-butyl esterification agent to obtain a compound of (1S,3R) configuration of the formula

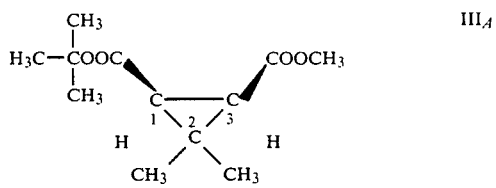

or a compound of (1R,3S) configuration of the formula

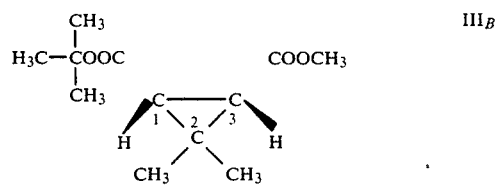

subjecting the said compound to selective hydrolysis to remove the methyl ester group to form a compound of the formula

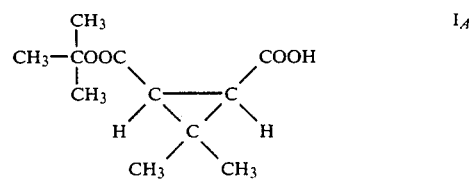

of (1S,3R) cis or (1R,3S) cis configuration, respectively and optionally subjecting the compound of formula $I_A$ to a strong isomerization base to obtain a compound of the formula

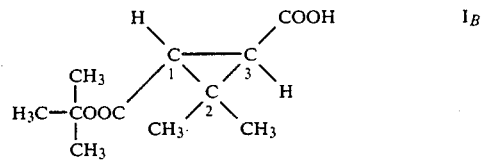

of (1R,3R) trans or (1S,3S) trans configuration which is a useful intermediate for the preparation of pesticidal compositions.

5 Claims, No Drawings

PROCESS FOR PREPARING CIS OR TRANS, OPTICALLY ACTIVE MONOALKYL ESTERS OF CYCLOPROPANE-1,3-DICARBOXYLIC ACIDS

PRIOR APPLICATIONS

This application is a continuation-in-part application of my copending commonly assigned U.S. patent applications Ser. No. 308,027 filed Oct. 2, 1981 now abandoned and Ser. No. 308,026 filed Oct. 2, 1981, now U.S. Pat. No. 4,408,066.

STATE OF THE ART

J.A.C.S., Vol. 76 (1954) p. 5257 describes the preparation of cis caronic acid by oxidation of a bicyclic diacetonic compound and gives physical constants for the corresponding methyl ester but the reference does not forsee the synthesis of the corresponding trans acid or its methyl ester. French Pat. No. 2,376,120 describes the preparation of alkyl esters of racemic 2,2-disubstituted-3-formyl-cyclopropane-1-carboxylic acids by reducing the acid function of a monoalkyl ester of the corresponding 2,2-disubstituted-cyclopropane-1,3-dicarboxylic acid followed by oxidation of the resulting alcohol group.

OBJECTS OF THE INVENTION

It is an object of the invention to provide a novel process for the preparation of the optically active forms of the compounds of formula I.

This and other objects and advantages of the invention will become obvious from the following detailed description.

THE INVENTION

The novel process of the invention for the preparation of esters of 2,2-dimethyl-cyclopropane-1,3-dicarboxylic acids in their optically active forms having a cis or trans configuration I comprising salifying the monomethyl ester of (1RS,3SR) cis 2,2-dimethyl-cyclopropane-1,3-dicarboxylic acid with d or l α-methyl-benzylamine, recovering the crystallized salt formed, dissolving the said salt in water, treating the solution with a mineral base and then with an acid to obtain either the monomethyl ester of (1R,3S) cis 2,2-dimethyl-cyclopropane-1,3-dicarboxylic acid I or its (1S,3R) cis isomer depending on whether d or l α-methyl-benzylamine, respectively was used, if desired, reacting the latter cis compound with a strong base to isomerize the monomethyl ester to the monomethyl ester of (1S,3S) trans 2,2-dimethyl-cyclopropane-1,3-dicarboxylic acid I or (1R,3R) trans isomer, respectively, or reacting the latter cis compound with a tert-butyl esterification agent to obtain a compound of (1S,3R) configuration of the formula

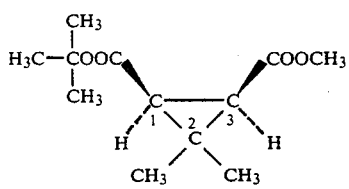

or a compound of (1R,3S) configuration of the formula

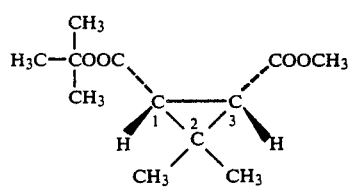

subjecting the said compound to selective hydrolysis to remove the methyl ester group to form a compound of the formula

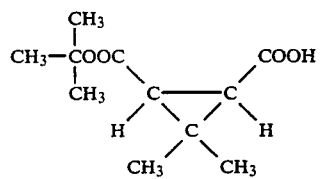

of (1S,3R) cis or (1R,3S) cis configuration, respectively and optionally subjecting the compound of formula $I_A$ to a strong isomerization base to obtain a compound of the formula

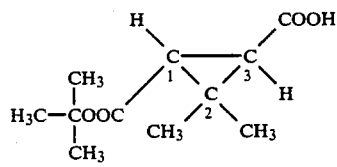

of (1R,3R) trans or (1S,3S) trans configuration which is a useful intermediate for the preparation of pesticidal compositions.

The process of the invention is illustrated in the following reaction scheme

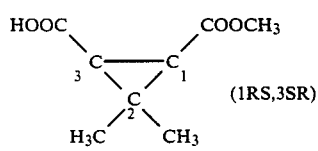

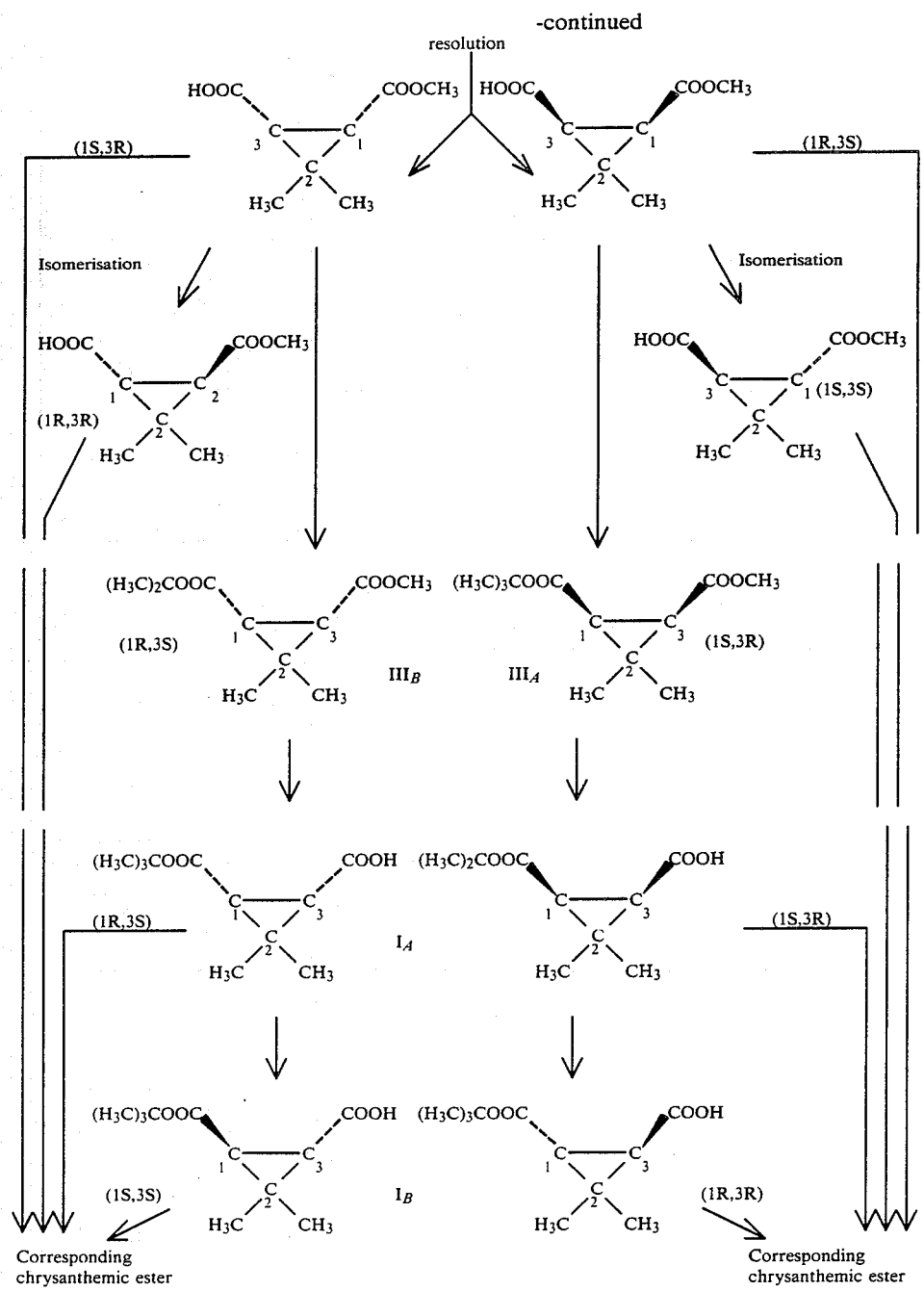

In a preferred mode of the process of the invention, the salification with α-methyl-benzylamine is effected in acetone and the crystallization of the salt from acetone is effected in 2 steps. The mineral base is preferably an alkali metal carbonate or hydroxide such as potassium carbonate, sodium carbonate, dilute sodium hydroxide solution and dilute potassium hydroxide solution. The acid used is preferably a dilute inorganic acid such as dilute hydrochloric acid or dilute sulfuric acid. The strong base for the isomerization is preferably an alkali metal alcoholate such as sodium methylate, sodium ethylate or potassium tert.-butylate or an alkali metal hydride and is effected in an alcohol or ether. Preferably, the tert.-butyl esterification agent is isobutene reacting with the monomethyl ester of (1R,3S)cis 2,2-dimethyl cyclopropane 1,3-dicarboxylic acid, or its (1S,3R) cis isomer, in the presence of an acid such as sulfuric acid in an organic solvent such as methylene chloride and the selective hydrolysis of the methyl ester group is effected with an inorganic base such as potassium carbonate in an aqueous alcoholic medium such as aqueous methanol. The strong base used for the isomerization is preferably an alkali metal alcoholate such as sodium methylate, sodium ethylate or potassium tert.-butylate in an alcohol or ether solvent.

A particular embodiment of the invention comprises salifying the monomethyl ester of (1RS,3SR) cis 2,2-dimethyl-cyclopropane-1,3-dicarboxylic acid with d or l α-methyl-benzylamine, recovering the crystallized salt formed, dissolving the said salt in water, treating the solution with a mineral base and then with an acid to obtain either the monomethyl ester of (1R,3S) cis 2,2-dimethyl-cyclopropane-1,3-dicarboxylic acid or its (1S,3R) cis isomer depending on whether d or l α-methyl-benzylamine, respectively was used, if desired, reacting the latter with a strong base to isomerize the monomethyl ester to the monomethyl ester of (1S,3S) trans 2,2-dimethyl-cyclopropane-1,3-dicarboxylic acid or (1R,3R) trans isomer, respectively.

Another particular embodiment of the invention comprises reacting the monomethyl ester of (1R,3S)cis 2,2-dimethyl cyclopropane 1,3-dicarboxylic acid, or its (1S,3R)cis isomer with a tert-butyl esterification agent to obtain a compound of (1S,3R) configuration of the formula

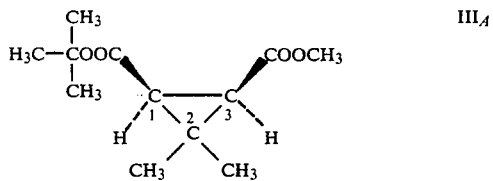

III$_A$ or a compound of (1R,3S) configuration of the formula

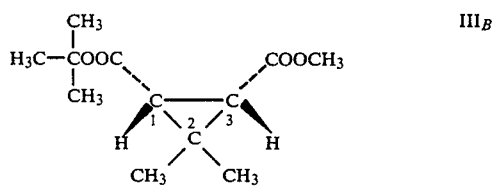

III$_B$ subjecting the said compound to selective hydrolysis to remove the methyl ester group to form a compound of the formula

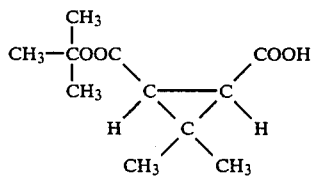

I$_A$ of (1S,3R) cis or (1R,3S) cis configuration, respectively and optionally subjecting the compound of formula I$_A$ to a strong isomerization base to obtain a compound of the formula

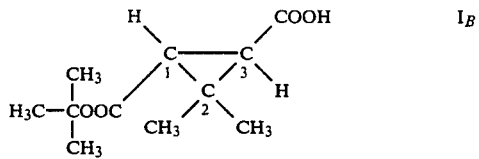

I$_B$ of (1R,3R) trans or (1S,3S) trans configuration, respectively.

Until now, the resolution of esters of cis cyclopropane-1,3-dicarboxylic acids was not known and the interest in such a process resides in the fact that the resolution which is not possible in the case of the dicarboxylic acids becomes possible in the case of the monomethyl esters due to the existence of enantiomers caused by dissymetry of the molecule.

Moreover, the conversion of a derivative of a cis cyclopropane-dicarboxylic acid to the corresponding trans derivative has not been previously known and the process of the invention shows, in an unexpected manner, that it is possible to isomerize a compound of formula I with a (1R,3S) cis or (1S,3R) cis configuration into the analogous (1S,3S) trans or (1R,3R) trans isomer by treatment with a strong base without saponification of the ester group or a racemization.

Until now, no process was known for a stereoselective transformation of cyclopropane dicarboxylic acid derivatives and the stereoselective transformation of the monomethyl ester of 2,2-dimethyl cyclopropane 1,3-dicarboxylic acid of (1R,3S) cis and (1S,3R) cis configuration to the respectively (1S,3R) cis and (1R,3S) cis compounds of formula I$_A$ is effected in an original manner as compared to those usually used for certain cyclopropanecarboxylic acid derivatives.

The process of the invention permits a simple stereoselective transformation taking advantage of derivatives of the dicarboxylic acid structure and a simple interconversion of the acid and ester groups leads to a desirable stereoselective transformation.

The compounds of formula I are useful intermediates and may be used in the synthesis of the corresponding chrysanthemic acid derivatives. It is possible to subject the compounds of formula I to a reduction of the acid function to the alcohol group, then oxidize the alcohol group to an aldehyde and subject the latter to the Wittig reaction with a triphenyl isopropyl phosphonium halide to obtain methyl or tert.-butyl chrysanthemate with the same configuration of the compound of formula I.

This series of reactions is illustrated in Example 5. French Pat. No. 2,376,120 illustrates a series of reactions of this type using racemic compounds.

It is well known that chrysanthemic acid esters are also useful as intermediates in the synthesis of other known esters possessing pesticidal activity such as insecticidal activity.

In the following examples there are described several preferred embodiments to illustrate the invention. However, it is to be understood that the invention is not intended to be limited to the specific embodiments.

EXAMPLE 1

Monomethyl ester of (1S,3R) cis and (1R,3S) cis 2,2-dimethyl-cyclopropane-1,3-dicarboxylic acid 3.7 g of d (+) α-methyl-benzylamine were added to a solution of 100 ml of acetone and 5.26 g of the monomethyl ester of (1RS,3SR) cis 2,2-dimethyl-cyclopropane-1,3-dicarboxylic acid and the mixture stood for 4 days at room tempera- and was then filtered to remove crystals. The filtrate was evaporated to dryness and the residue was taken up in acetone. The solution was allowed to stand for 24 hours and was then filtered. The two groups of crystals were combined and the filtrate A was kept.

The crystals were dissolved in acetone and after initialization of crystallization, the mixture was allowed to stand for 3 days. The mixture was filtered and the crystals were dried to obtain 1.69 g of the benzylamine salt which was then dissolved in water. 1.03 g of potassium carbonate were added to the solution and the aqueous phase was washed with ether and was slightly acidified by addition of 10% hydrochloric acid solution. The mixture was extracted with ether and the ether phase was washed with water, then with aqueous sodium chloride solution, dried and evaporated to dryness to obtain 1 g of the monomethyl ester of (1R,3S) cis 2,2-dimethylcyclopropane-1,3-dicarboxylic acid with a melting point of 54° C. and a specific rotation of $[\alpha]_D^{25} = +30.92°$ (c=ethanol) which shows that the product consisted of 5.77% of the (1S,3R) cis isomer and 94.23% of the (1R,3S) cis isomer having the formula

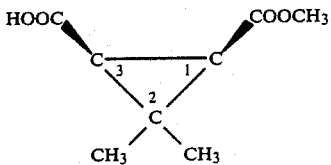

Filtrate A was evaporated to dryness and the crystalline material was treated as above to obtain a product consisting of 43% of the monomethyl esters of (1R,3S)cis 2,2-dimethyl-cyclopropane-1,3-dicarboxylic acid and 57% of the (1S,3R)cis isomer of the formula

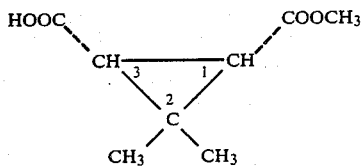

2.56 g of this above mixture and 1.8 g of 1 (−) α-methyl-benzylamine were reacted as above to obtain 0.813 g of the monomethyl ester of (1S,3R)cis 2,2-dimethyl-cyclopropane-1,3-dicarboxylic acid with a melting point of 53° C. and a specific rotation of $[\alpha]_D^{25} = -29.35°$ (c=ethanol) which was 92% of the (1S,3R)cis isomer and 8% of the (1R,3S)cis isomer.

NMR Spectrum (deuterochloroform): (1S,3R)cis isomer

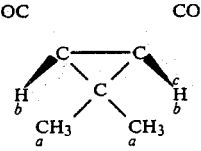

ΔH$_a$ = singulet at 1.28 ppm and at 1.40 ppm
ΔH$_b$ = singulet at 1.96 ppm
ΔH$_c$ = singulet at 3.70 ppm

EXAMPLE 2

Step A: Tert.-butyl ester of (1R,3S)cis 2,2-dimethyl-1-methoxycarbonyl-cyclopropane-3-carboxylic acid.

A few drops of sulfuric acid were added to a solution of 0.516 g of the monomethyl ester of (1S,3R)cis 2,2-dimethyl-cyclopropane-1,3-dicarboxylic acid in 10 ml of methylene chloride and a current of isobutene was passed through the solution for 45 minutes. A saturated sodium bicarbonate solution was added to the mixture which was then extracted with ether. The ether phase was washed with water, then with aqueous sodium chloride solution, dried and evaporated to dryness to obtain 0.51 g of tert.-butyl ester of (1R,3S)cis 2,2-dimethyl-1-methoxycarbonyl-cyclopropane-3-carboxylic acid with a specific rotation of $[\alpha]_D^{25} = -22.06°$ (in acetone)

NMR Spectrum (deuterochloroform)

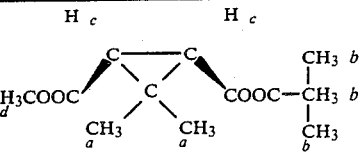

ΔH$_a$ = singulet at 1.16 ppm and 1.29 ppm
ΔH$_b$ = singulet at 1.35 ppm
ΔH$_c$ = singulet at 1.66 ppm
ΔH$_d$ = singulet at 3.56 ppm Analysis:
| | | % C | 63.14 | % H | 8.83 |
|---|---|---|---|---|---|
| Calculated: | | | | | |
| Found: | | | 63.5 | | 8.8 |

Step B: Mono tert.-butyl ester of (1R,3S)cis 2,2-dimethyl-cyclopropane-1,3-dicarboxylic acid 1.27 g of potassium carbonate were added to a solution of 0.42 g of the product of Step B in 7 ml of a 1—1 methanol-water mixture and the mixture was refluxed for 16 hours and then cooled to room temperature. 10% hydrochloric acid was added to the mixture to adjust the pH to 2 and the mixture was extracted with ether. The organic phase was washed with water, then with aqueous saturated sodium chloride solution, was dried and evaporated to dryness. The residue was chromatographed over silica gel and was eluted with ether to obtain 0.31 g of mono-tert.-butyl ester (1R,3S)cis 2,2-dimethyl-cyclopropane-1,3-dicarboxylic acid with an Rf=0.85 and a specific rotation of $[\alpha]_D^{20} = +1.78°$ (ethanol) and having a melting point of 114° C.

IR Spectrum: Absorption at 2400 to 3600$cm^{-1}$ (OH); at 1720$cm^{-1}$ (ester carbonyl); at 1705$cm^{-1}$(acid carbonyl).

NMR Spectrum (deuterochloroform):

ΔH$_a$ = singulet at 1.24 ppm and 1.36 ppm
ΔH$_b$ = singulet at 1.42 ppm
ΔH$_c$ = singulet at 1.87 ppm
ΔH$_d$ = massive center towards 10.7 ppm

EXAMPLE 3

Mono tert.-butyl ester of (1S,3S) trans 2,2-dimethyl-cyclopropane-1,3-dicarboxylic acid A mixture of 0.64 g of the monotert.-butyl ester of (1R,3S)cis 2,2-dimethyl-cyclopropane-1,3-dicarboxylic acid and 3 ml of 5M sodium methylate in methanol was refluxed under an inert gas for 75 minutes and was cooled to room temperature. The pH of the mixture was adjusted to 2 by addition of 10% hydrochloric acid and the mixture was extracted with ether. The organic phase was washed with water, then with aqueous saturated sodium chloride solution, was dried and evaporated to dryness to obtain 0.35 g of mono tert.-butyl ester of (1S,3S) trans 2,2-dimethyl-cyclopropane-1,3-dicarboxylic acid melting at 105° C.

IR Spectrum: Absorption at 2400 to 3680$^{cm-1}$ (OH); at 1720$^{cm-1}$ (ester carbonyl); and at 1700$^{cm-1}$ (acid carbonyl).

NMR Spectrum (deuterochloroform):

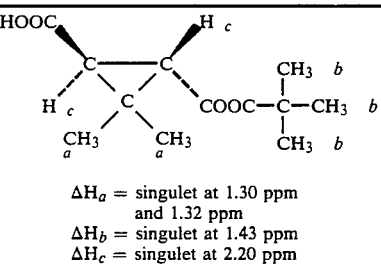

$\Delta H_a$ = singulet at 1.30 ppm and 1.32 ppm
$\Delta H_b$ = singulet at 1.43 ppm
$\Delta H_c$ = singulet at 2.20 ppm

EXAMPLE 4

Mono tert.-butyl ester of (1S,3R)cis 2,2-dimethyl-cyclopropane 1,3-dicarboxylic acid Step A:

Using the procedure of Step A of Example 2, the monomethyl ester of (1R,3S)cis 2,2-dimethyl-cyclopropane-1,3-dicarboxylic acid was reacted with isobutene to form the corresponding tert.-butyl ester of (1S,3R) cis 2,2-dimethyl-1-methoxycarbonyl-cyclopropane-3-carboxylic acid.

NMR Spectrum (deuterochloroform):

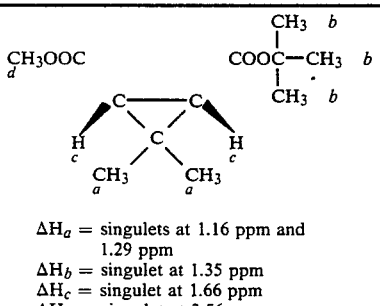

$\Delta H_a$ = singulets at 1.16 ppm and 1.29 ppm
$\Delta H_b$ = singulet at 1.35 ppm
$\Delta H_c$ = singulet at 1.66 ppm
$\Delta H_d$ = singulet at 3.56 ppm Step. B:

Using the procedure of Step B of Example 2, the product of Step A was subjected to selective hydrolysis to form mono tert.-butyl ester of (1S,3R)cis 2,2-dimethyl-cyclopropane-1,3-dicarboxylic acid with a specific rotation of $[\alpha]_D^{20} = -1.8°$ (ethanol).

EXAMPLE 5

Mono tert.-butyl ester of (1R,3R)trans 2,2-dimethyl-cyclopropane-1,3-dicarboxylic acid A mixture of 0.21 g of the mono-tert.-butyl ester of (1S,3R)cis 2,2-dimethyl-cyclopropane-1,3-dicarboxylic acid, 4.5 ml of tertrahydrofuran and 0.31 g of potassium tert.-butylate was refluxed under an inert gas for one hour and the temperature was returned to room temperature. A 10% hydrochloric acid solution was added thereto and the mixture was extracted with ether. The ether phase was washed with water, then with an aqueous saturated sodium chloride solution, dried and evaporated to dryness to obtain 0.13 g of mono tert.-butyl ester of (1R,3R)trans 2,2-dimethyl-cyclopropane-1,3-dicarboxylic acid with a specific rotation of $[\alpha]_D^{20} = -29.90°$ (ethanol).

EXAMPLE 6

Mono methyl ester of (1R,3R) trans 2,2-dimethyl cyclopropane 1,3-dicarboxylic acid A mixture of 0.516 g of the monomethyl ester of (1S,3R)cis 2,2-dimethyl-cyclopropane-1,3-dicarboxylic acid and 3 ml of a solution of 5M sodium methylate in methanol was refluxed under an inert gas for 75 minutes and was then cooled to room temperature. 10% hydrochloric acid was added to the mixture to adjust the pH to 2 and the mixture was then extracted with ether. The organic phase was washed with water and then with aqueous saturated sodium chloride solution, dried and evaporated to dryness to obtain 0.36 g the monomethyl ester of (1R,3R)trans 2,2-dimethyl-cyclopropane-1,3-dicarboxylic acid with a specific rotation of $[\alpha]_D^{25} = -51.65°$ C. (c=ethanol). The isomerization was effected by the following reaction.

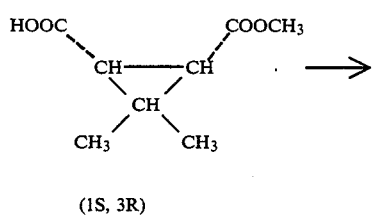

(1S, 3R)

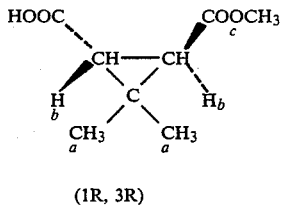

(1R, 3R)

NMR Spectrum (deuterochloroform): $\Delta H_a$=singulet at 1.28 ppm and at 1.31 ppm; $\Delta H_b$=singulet at 2.23 ppm; $\Delta H_c$=singulet at 3.70 ppm.

EXAMPLE 7

Mono methyl ester of (1S,3S) trans 2,2-dimethyl cyclopropane 1,3-dicarboxylic acid Using the procedure of Example 5, the monomethyl ester of (1R,3S)cis 2,2dimethyl-cyclopropane-1,3-dicarboxylic acid was reacted to obtain the monomethyl ester of (1S,3S) trans 2,2-dimethyl-cyclopropane-1,3-dicarboxylic acid with a specific rotation of $[\alpha]_D^{25} = +51.66°$ (c=ethanol). The reaction proceded according to the reaction scheme

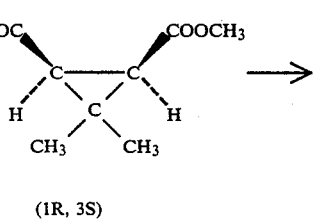

(1R, 3S)

-continued

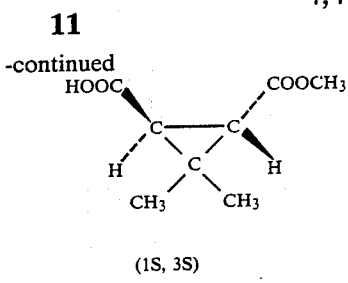

(1S, 3S)

EXAMPLE 8

Methyl (1R,3S) cis chrysanthemate

Step A: Methyl (1R,3S)cis 2,2-dimethyl-3-hydroxymethyl-cyclopropane-1-carboxylate 0.348 g of diborane in dimethyl sulfide ($5.05 \times 10^{-3}$ moles) were added slowly under an inert atmosphere to a solution of 0.8 g of the monomethyl ester of (1R,3S)cis 2,2-dimethyl-cyclopropane-1,3-dicarboxylic acid in 20 ml of ether and the mixture was refluxed for one hour and then cooled to room temperature. 2 ml of methanol and then 10 ml of 10% hydrochloric acid were added to the mixture which was extracted with ether. The ether phase was washed with water, then aqueous saturated sodium chloride solution, dried and evaporated to dryness. The residue was chromatographed over silica gel and was eluted with ether to obtain 0.57 g of methyl (1R,3S) cis 2,2-dimethyl-3-hydroxymethyl-cyclopropane-1-carboxylate as the fraction with an Rf=0.7. The product had a specific rotation of $[\alpha]_D^{25} = -73.76°$ (c=ethanol).

IR Spectrum (ethanol): Absorption at 3050 to $3700^{cm-1}$ (OH).

NMR Spectrum (chloroform):

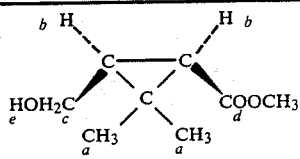

$\Delta H_a$ = singulet at 1.16 ppm
$\Delta H_b$ = multiplet of 1.24 to 1.56 ppm
$\Delta H_c$ = massive at 3.20 ppm
$\Delta H_d$ = singulet at 3.57 ppm
$\Delta H_e$ = doublet center towards 3.78 ppm (J = 7Hz)

Step B: Methyl (1R,3S)cis 2,2-dimethyl-3-formyl-cyclopropane-1-carboxylate

A solution of 0.54 g of the product of Step A in 7 ml of methylene chloride was added to a suspension of 1.105 g of a complex of chromic anhydride and pyridine hydrochloride ($5.18 \times 10^{-3}$ mole) in 7 ml of methylene chloride and the mixture was stirred for 3 hours. 7 ml of ether were added to the mixture which was stirred for 2 hours and was filtered. The filter was washed several times with ether and the filtrate was evaporated to dryness. The residue was chromatographed over silica gel and was eluted with an 8-2 ether-pentane mixture to recover 0.48 g of methyl (1R,3S)cis 2,2-dimethyl-3-formyl-cyclopropane-1-carboxylate with an Rf=0.85 and a specific rotation of $[\alpha]_D^{25} = -82.15°$ (c=acetone).

IR Spectrum (Chloroform): Absorption at $1730^{cm-1}$ (ester carbonyl); at $1700^{cm-1}$ (aldehyde carbonyl).

NMR Spectrum (chloforom):

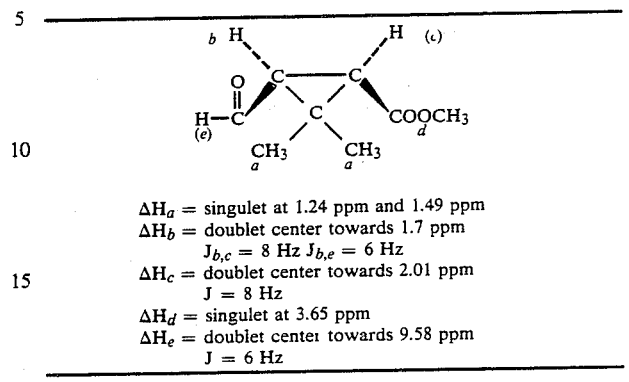

$\Delta H_a$ = singulet at 1.24 ppm and 1.49 ppm
$\Delta H_b$ = doublet center towards 1.7 ppm
  $J_{b,c}$ = 8 Hz  $J_{b,e}$ = 6 Hz
$\Delta H_c$ = doublet center towards 2.01 ppm
  J = 8 Hz
$\Delta H_d$ = singulet at 3.65 ppm
$\Delta H_e$ = doublet center towards 9.58 ppm
  J = 6 Hz

Step C: Methyl (1R,3S)cis chrysanthemate 1.5 ml of a solution of 1.6N butyllithium in hexane were added under an inert atmosphere to a suspension of 1.08 g of isopropyl triphenyl phosphonium iodide in 10 ml of tetrahydrofuran and the mixture was stirred for 10 minutes. Then, 0.34 g of the product of Step A were added to the mixture which was then stirred for 30 minutes and admixed with water. The mixture was extracted with ether and the organic phase was washed with water, then with aqueous saturated sodium chloride solution, dried and evaporated to dryness. The residue was chromatographed over silica gel and was eluted with a 1-9 ether-pentane mixture to obtain 0.19 g of methyl (1R,3S)cis chrysanthemate with an Rf=0.75 and a specific rotation of $[\alpha]_D^{25} = +57.840$ (c=acetone).

Various modifications of the products and process of the invention may be made without departing from the spirit or scope thereof and it is to be understood that the invention is intended to be limited only as defined in the appended claims.

What I claim is:

1. A process for the preparation of esters of 2,2-dimethyl-cyclopropane-1,3-dicarboxylic acids in their optically active forms having a cis or trans configuration comprising salifying the monomethyl ester of (1RS,3SR) cis 2,2-dimethyl-cyclopropane-1,3-dicarboxylic acid with d or l α-methyl-benzylamine, recovering the crystallized salt formed, dissolving the said salt in water, treating the solution with a mineral base and then with an acid to obtain either the monomethyl ester of (1R,3S) cis 2,2-dimethyl-cyclopropane-1,3-dicarboxylic acid I or its (1S,3R) cis isomer depending on whether d or l α-methyl-benzylamine, respectively was used and optionally reacting the latter cis compound with a strong base to isomerize the monomethyl ester to the monomethyl ester of (1S,3S) trans 2,2-dimethyl-cyclopropane-1,3-dicarboxylic acid I or (1R,3R) trans isomer.

2. The process of claim 1 wherein the salification with α-methyl-benzylamine is effected in acetone and the crystallization of the salt from acetone is effected in 2 steps, the mineral base is an alkali metal carbonate or dilute alkali metal hydroxide and the strong base is an alkali metal alcoholate or an alkali metal hydride.

3. A process for the preparation of esters of 2,2-dimethylcyclopropane-1,3-dicarboxylic acids in their optically active forms, having a cis or trans configuration I comprising salifying the monomethyl ester of (1RS,3SR) cis 2,2-dimethyl-cyclopropane-1,3-dicarboxylic acid with d or l α-methyl-benzylamine, recovering the crystallized salt formed, dissolving the said salt in water, treating the solution with a mineral base and then with an acid to obtain either the monomethyl ester of (1S,3S) cis 2,2-dimethyl-cyclopropane-1,3-dicarboxylic acid or its (1S,3R) cis isomer depending on whether d or l α-methyl-benzylamine, respectively was used, reacting the cis compound of (1R,3S) or (1S,3R) configuration with isobutene to obtain a compound of (1S,3R) configuration of the formula

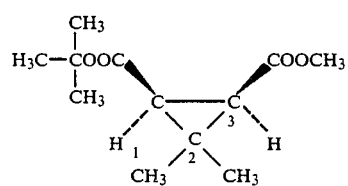

or a compound of (1R,3S) configuration of the formula

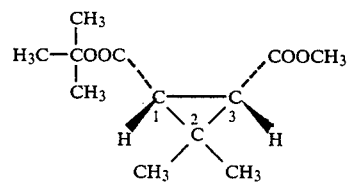

subjecting the said compound to selective hydrolysis to remove the methyl ester group to form a compound of the formula

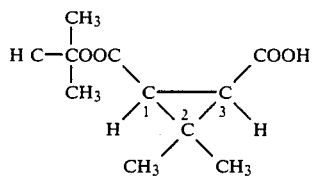

of (1S,3S) cis or (1R,3S) cis configuration, respectively and optionally subjecting the compound of formula $I_A$ to a strong isomerization base to obtain a compound of the formula

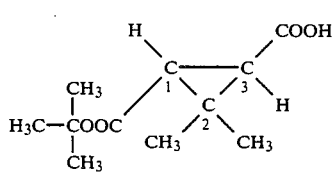

of (1R,3R) trans of (1S,3S) trans configuration.

4. The process of claim 3 wherein the reaction with isobutene is effected in the presence of an acid in an organic solvent and the selective hydrolysis is effected with an inorganic base in an aqueous alcoholic medium and the strong base is an alkali metal alcoholate.

5. The process of claim 3 wherein the reaction with isobutene is effected in the presence of sulfuric acid in methylene chloride, the selective hydrolysis is effective with potassium carbonate in aqueous methanol and the strong base is sodium methylate, sodium ethylate or potassium tert.-butylate in an alcohol or ether.

* * * * *